United States Patent
Justis et al.

(10) Patent No.: US 8,292,934 B2
(45) Date of Patent: Oct. 23, 2012

(54) DYNAMIC ANCHOR ASSEMBLY FOR CONNECTING ELEMENTS IN SPINAL SURGICAL PROCEDURES

(75) Inventors: Jeff Justis, Germantown, TN (US); Jonathan Dewey, Sunnyvale, CA (US); Dimitri Protopsaltis, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 526 days.

(21) Appl. No.: 12/253,644

(22) Filed: Oct. 17, 2008

(65) Prior Publication Data
US 2010/0100137 A1 Apr. 22, 2010

(51) Int. Cl.
*A61B 17/04* (2006.01)

(52) U.S. Cl. ......... 606/328; 606/264; 606/305; 606/308

(58) Field of Classification Search ............. 606/53, 606/60, 61, 65, 72, 73, 303; 623/17, 17.11–17.16
See application file for complete search history.

(56) References Cited

U.S. PATENT DOCUMENTS

| | | | | |
|---|---|---|---|---|
| 5,536,268 | A * | 7/1996 | Griss | 606/254 |
| 5,882,350 | A * | 3/1999 | Ralph et al. | 606/278 |
| 5,964,760 | A | 10/1999 | Richelsoph | |
| 6,565,565 | B1 * | 5/2003 | Yuan et al. | 606/272 |
| 6,740,086 | B2 | 5/2004 | Richelsoph | |
| 7,087,057 | B2 | 8/2006 | Konieczynski et al. | |
| 7,141,051 | B2 | 11/2006 | Janowski et al. | |
| 7,261,714 | B2 | 8/2007 | Richelsoph | |
| 7,316,684 | B1 | 1/2008 | Baccelli et al. | |
| 2003/0199873 | A1 | 10/2003 | Richelsoph | |
| 2004/0153068 | A1 | 8/2004 | Janowski et al. | |
| 2004/0193160 | A1 | 9/2004 | Richelsoph | |
| 2004/0225289 | A1 | 11/2004 | Biedermann et al. | |
| 2004/0267264 | A1 * | 12/2004 | Konieczynski et al. | 606/73 |
| 2005/0154390 | A1 | 7/2005 | Biedermann et al. | |
| 2005/0203516 | A1 | 9/2005 | Biedermann et al. | |
| 2005/0216003 | A1 * | 9/2005 | Biedermann et al. | 606/61 |
| 2005/0228382 | A1 | 10/2005 | Richelsoph et al. | |
| 2005/0277928 | A1 * | 12/2005 | Boschert | 606/61 |
| 2006/0129147 | A1 | 6/2006 | Biedermann et al. | |
| 2006/0149241 | A1 | 7/2006 | Richelsoph et al. | |
| 2006/0241599 | A1 | 10/2006 | Konieczynski et al. | |
| 2006/0241618 | A1 | 10/2006 | Gasser et al. | |
| 2006/0293666 | A1 | 12/2006 | Matthis et al. | |
| 2007/0043364 | A1 | 2/2007 | Cawley et al. | |
| 2007/0055235 | A1 | 3/2007 | Janowski et al. | |
| 2007/0093832 | A1 * | 4/2007 | Abdelgany | 606/61 |
| 2007/0173817 | A1 | 7/2007 | Sournac et al. | |
| 2007/0173819 | A1 | 7/2007 | Sandlin | |

FOREIGN PATENT DOCUMENTS

| | | |
|---|---|---|
| EP | 0807420 A1 | 11/1997 |
| WO | WO9702786 A1 | 1/1997 |
| WO | 2007067443 A2 | 6/2007 |

OTHER PUBLICATIONS

International Search Report and Written Opinion for U.S. Application No. PCT/US2009/060835 mailed on Jan. 11, 2010.

* cited by examiner

*Primary Examiner* — Thomas Barrett
*Assistant Examiner* — Melissa A Golob

(57) ABSTRACT

Devices and methods include a multi-axial anchor assembly engageable to a vertebra and a connecting element positionable through a receiver of the anchor assembly. The anchor assembly includes a flexible member between the receiver and an anchor member of the anchor assembly, thereby providing a flexible joint in the anchor assembly for allowing limited movement after primary multi-axial capability between the receiver and the anchor member has been arrested.

29 Claims, 13 Drawing Sheets

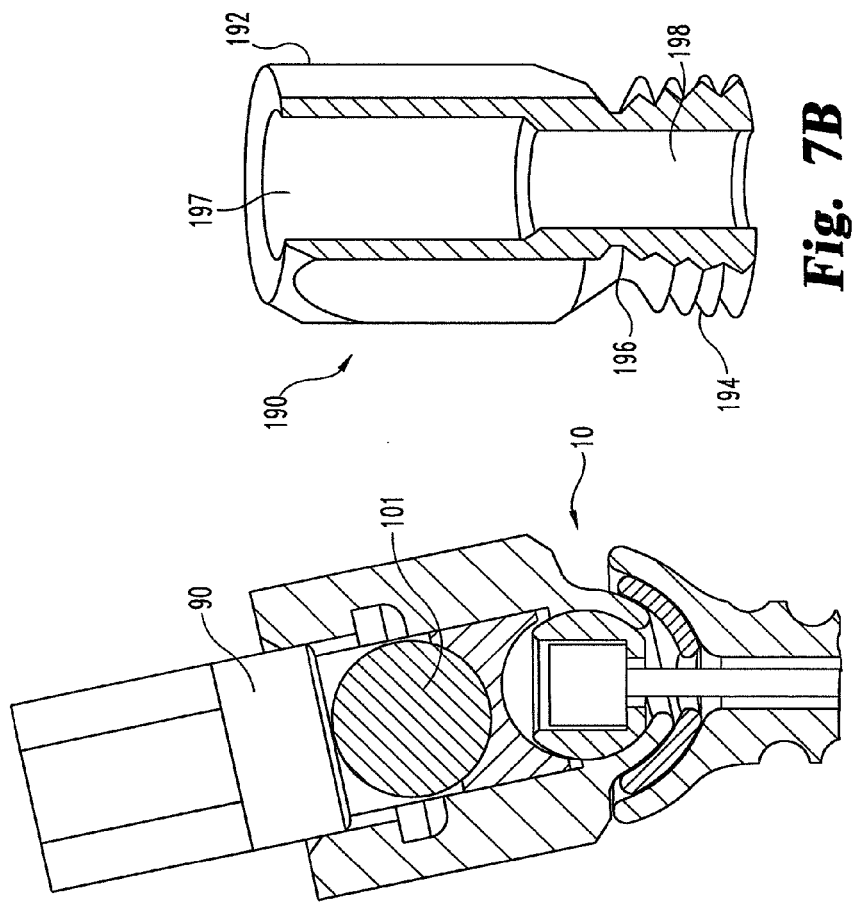
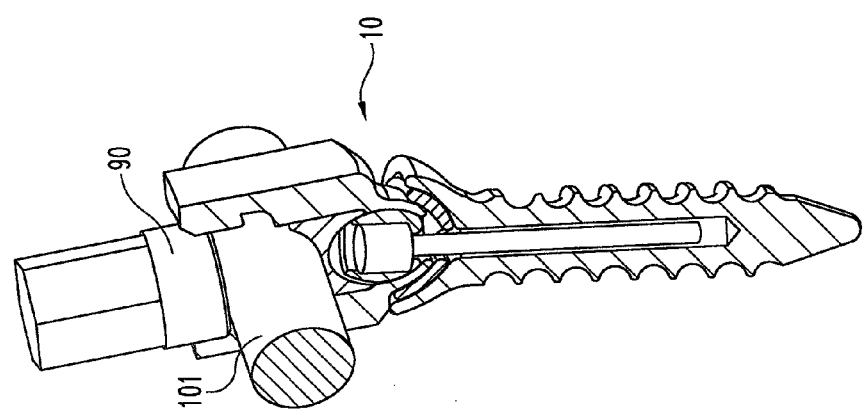

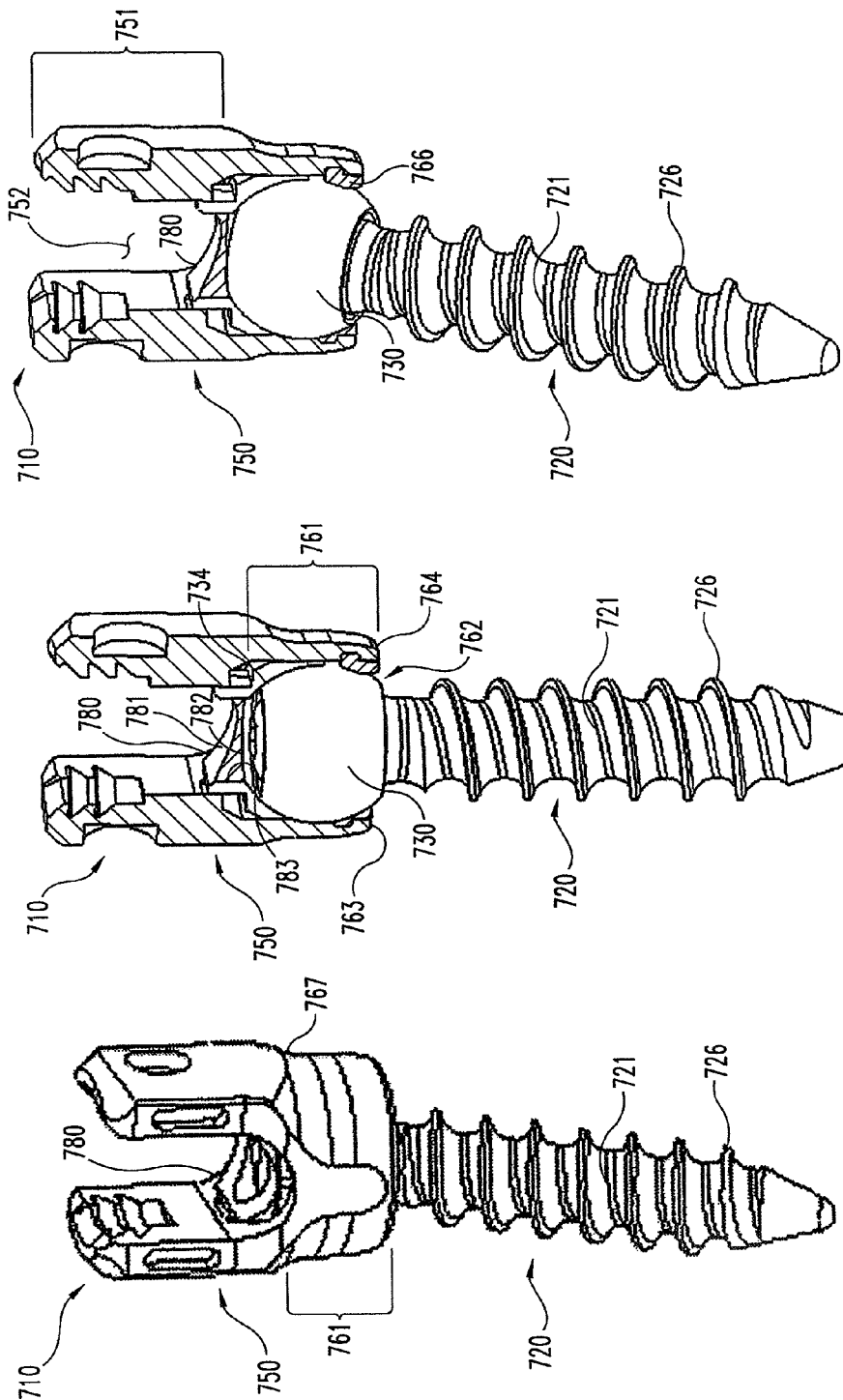

DYNAMIC ANCHOR ASSEMBLY FOR CONNECTING ELEMENTS IN SPINAL SURGICAL PROCEDURES

BACKGROUND

Spinal implants can be engaged to or along one or more vertebrae of the spinal column for the treatment of various spinal conditions. For example, elongated connecting elements, such as rods, plates, tethers, wires, cables, and other devices have been implanted along the spinal column and connected between two or more anchors engaged between one or more spinal motion segments. Fasteners can be provided to secure the implant to a particular location along the spinal column. The implants can be provided to stabilize the spinal column for treatment, either by fixing the spinal column or by permitting at least some motion of the stabilized motion segments.

Anchor assemblies such as multi-axial and uni-axial screws have been employed for securing elongated implants, such as rods or plates, along one or more motion segments of the spinal column. Such screws can comprise many components or parts to secure the implant to the screw, and such components can interact with one another and with the screw shaft to allow angular movement relative to the shaft for orienting the assembly into proper alignment with the elongate implant, and then cooperate with one another to rigidly lock the elongate implant into a fixed position relative to the screw shaft. The interaction between the components of these screws and the elongated implant and the complex spinal anatomy can result in less than optimal outcomes, some of which relate to stresses that are placed on the anchor after implantation, for example, resulting from normal activity of the patient. Dynamic anchor assemblies that allow movement of assembly components coupled to elongate members relative to assembly components coupled to bony structures of the patient after locking the assembly to elongate members are needed.

SUMMARY

The present invention generally relates to bone anchor assemblies, and devices and methods for securing connecting elements with bone anchor assemblies.

In one form, an attachment apparatus for attaching an elongated connecting element to a vertebral column includes an anchor member engageable to a vertebral body; a receiver defining a channel configured to receive and engage an elongated connecting element; and a flexible member positioned at an interface between said receiver and said anchor member. The anchor member including a distal bone engaging portion and a proximal end portion configured to extend from the surface of the vertebral body. In one embodiment, the proximal end portion of the anchor member has a convex or concave proximal surface; the receiver has a concave or convex distal surface having a contour complementary to the proximal surface of the anchor member; and the flexible member is positioned between the distal surface of the receiver and the proximal surface of the anchor member. In this embodiment, the attachment apparatus further includes a component for attaching the receiver to the anchor member in an orientation whereby the distal surface of the receiver faces the proximal surface of the anchor member in an opposing relationship spaced apart by the flexible member. In another embodiment, the distal surface of the receiver and the proximal surface of the anchor member provide an interface between the receiver and the anchor member that allows multi-axial motion of the receiver relative to the anchor member.

In another embodiment attachment apparatus the component for attaching the receiver to the anchor member comprises a tether. The component can also include a ferrule defining a bore therethrough and having a spherical outer surface dimensioned to be seated in a complementary cavity in the receiver. A shaft portion of the tether can extend distally from the bore of the ferrule and can be captured in an axial chamber formed in the anchor member that extends from and opens through the proximal end of the bone anchor. The bore can be configured to capture a head portion of the tether, thereby attaching the receiver to the bone anchor.

In yet another embodiment attachment apparatus, the flexible member comprises an annular body disposed about the proximal head portion of the anchor member; and the apparatus further includes a collar disposed about the flexible member, the collar having a semi-spherical outer surface configured to be coupled to the receiver.

In another form, a system for stabilizing a bony segment includes an elongated connecting element and an anchoring assembly engageable to the connecting element. The anchoring assembly includes an anchor member engageable to the bony segment, a receiver member that is coupled to the anchor member and extends proximally therefrom along a receiver axis, a flexible member positioned at an interface between the receiver and the anchor member and a securing member engageable to the receiver member to secure the connecting element in the receiver member. The receiver member defines a channel for receiving the connecting element along any one of a plurality of implantation axes that are transverse to the receiver axis.

In yet another form, a spinal stabilization system includes an anchor member engageable to a vertebral body, the anchor member including a distal bone engaging portion and a proximal end portion configured to extend from the surface of the vertebral body; a receiver defining a cavity configured to receive and engage an elongated connecting element; means for engaging the receiver to the anchor member, the engaging means comprising a flexible member effective to allow limited movement of the receiver relative to the anchor; and an elongated connecting element received in the cavity of the receiver.

In another aspect, a method for stabilizing a spinal column segment comprises: (1) engaging an anchor assembly to a vertebra of the spinal column, the anchor assembly comprising a receiver, an anchor member with a distal bone engaging portion extending distally and axially from the receiver and a flexible member positioned at an interface between the receiver and the anchor member; (2) pivoting the receiver to orient the longitudinal axis in a desired position relative to the distal bone engaging portion; (3) inserting a connecting element into the recess of the receiver so that the connecting element extends from the receiver; and (4) retaining the connecting element distally and proximally within the receiver.

In yet another aspect, an attachment apparatus for attaching an elongated connecting element to a vertebral column includes an anchor member engageable to a vertebral body, the anchor member including a distal bone engaging portion and a proximal end portion configured to extend from the surface of the vertebral body; a receiver defining a cavity configured to receive and engage an elongated connecting element; and a tether movably connecting the receiver to the anchor member.

These and other aspects will be discussed further below.

BRIEF DESCRIPTION OF THE DRAWINGS

FIG. 6 is a perspective view in partial section of the anchor assembly of FIG. 2 with a connecting element coupled to receiver.

FIG. 7A is an elevation view in partial section of the anchor assembly of FIG. 2 with a connecting element coupled to receiver.

FIG. 7B is a perspective view of an engaging member embodiment engageable with the receiver to secure a connecting element in the receiver.

FIG. 15 is a perspective view of another embodiment anchor assembly.

FIG. 16 is a perspective view in partial section of the anchor assembly of FIG. 15 with receiver in a first position relative to anchor member.

FIG. 17 is a perspective view in partial section of the anchor assembly of FIG. 15 with receiver in a second position relative to anchor member.

DESCRIPTION OF THE ILLUSTRATED EMBODIMENTS

Figure 1:
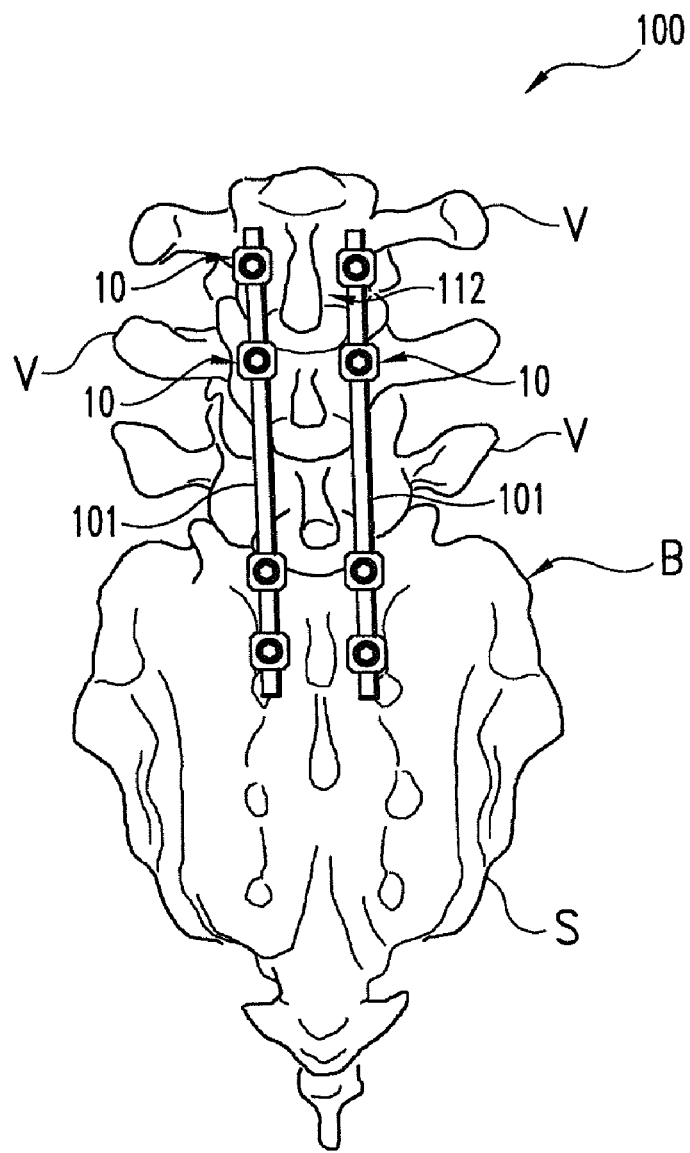
FIG. 1 is a posterior elevation view of a spinal column segment and spinal implant system.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Devices and methods for facilitating placement and securement of a connecting element between anchor assemblies are provided for spinal surgical procedures. The anchor assemblies discussed herein include an anchor member engageable to a vertebra and a receiver for receiving a connecting element. In one embodiment, the anchor assemblies include an anchor member configured to rigidly engage a bony structure, a receiver configured to engage the anchor member and defining a recess and configured to receive and capture the connecting element in the recess, and a flexible member positioned between the anchor member and the receiver. The manner of coupling the receiver to the anchor member allows multiaxial movement of the receiver relative to the anchor member, providing for the anchor member to be positioned at various angles relative to the receiver prior to the time the connecting element is captured in the recess and thereby attached to the receiver. After the connecting element is captured in the recess and thereby attached to the receiver, the receiver is locked into a fixed position relative to the anchor member, with the flexible member positioned at an interface therebetween. As used herein, the words "fixed positioning" refer to the positioning of the receiver and anchor member in an unstressed condition. The presence of the flexible member between the receiver and the anchor member, however, allows for some limited relative movement between the receiver and the anchor member after the connecting element has been captured in the recess and attached to the connecting element. In one form, as further described hereinbelow, an engaging member is engageable to the receiver to secure the connecting element with the anchor assembly; however, it is understood that some embodiments, such as, for example, embodiments in which the receiver has a "closed" form, do not require an engaging member.

The anchor member of the anchor assembly includes a distal lower portion that is engageable to a vertebral body with the proximal receiver positioned adjacent the vertebra. The anchor member can extend along the longitudinal axis of the receiver to minimize the footprint of the anchor assembly and minimize intrusion into adjacent tissue. In one embodiment, the anchor member is in the form of a bone screw with a threaded shaft and a proximal head that is pivotally captured in or otherwise attached to the receiver. In other embodiments, the distal anchor member can be in the form of a hook, staple, cable, tether, suture anchor, interbody fusion implant, artificial disc implant, bolt, or other structure engageable to bony tissue. The receiver defines a passage that receives a connecting element, such as a rod, tether, wire, cable, plate or other elongated connecting element that can extend between one or more additional anchor assemblies secured to one or more additional vertebrae.

FIG. 1 illustrates a posterior spinal implant system 100 located along a spinal column of a patient. More specifically, implant system 100 can be affixed to bones B of the spinal column segment 112 from a posterior approach. Bones B can include the sacrum S and several vertebrae V. Implant system 100 generally includes several bone anchor assemblies 10 and elongated connecting elements 101 structured to selectively interconnect with bone anchor assemblies 10. Connecting elements 101 may be a spinal rod, plate, bar, or other elongated element having a length to extend between at least two vertebrae. Connecting element 101 may be solid or hollow along some or all of its length and/or may be of homogenous or heterogeneous composition. In implant system 100, bone anchor assemblies 10 are affixed to various locations of the spinal column segment 112 and interconnected with connecting elements 101. Spinal implant system 100 may be used for, but is not limited to, treatment of degenerative spondylolisthesis, fracture, dislocation, scoliosis, kyphosis, spinal tumor, and/or a failed previous fusion.

FIGS. 2-8C show anchor assembly 10 in further detail. Anchor assembly 10 includes an anchor member 20 pivotally coupled to receiver 50 with a flexible member 40 positioned at an interface between receiver 50 and the proximal end of anchor member 20, with anchor member 20 extending distally from receiver 50. Anchor member 20 includes an elongated shaft 21 extending along a longitudinal axis 22 and an enlarged proximal end portion 23 having a concave surface 24 at the proximal end of shaft 21 that defines a cavity 25 for receiving a complimentary surface of receiver 50. Shaft 21 can include an outer thread profile 26 for threadingly engaging a bony structure to secure anchor assembly 10 thereto. In addition, enlarged proximal end portion 23 can include external surface features (not shown) to allow gripping of anchor member 20 by a driving tool (not shown) to facilitate engagement of shaft 21 to the bony structure. Shaft 21 also defines an internal chamber 27 that opens through surface 24 for receiving tether 75.

Figure 2:
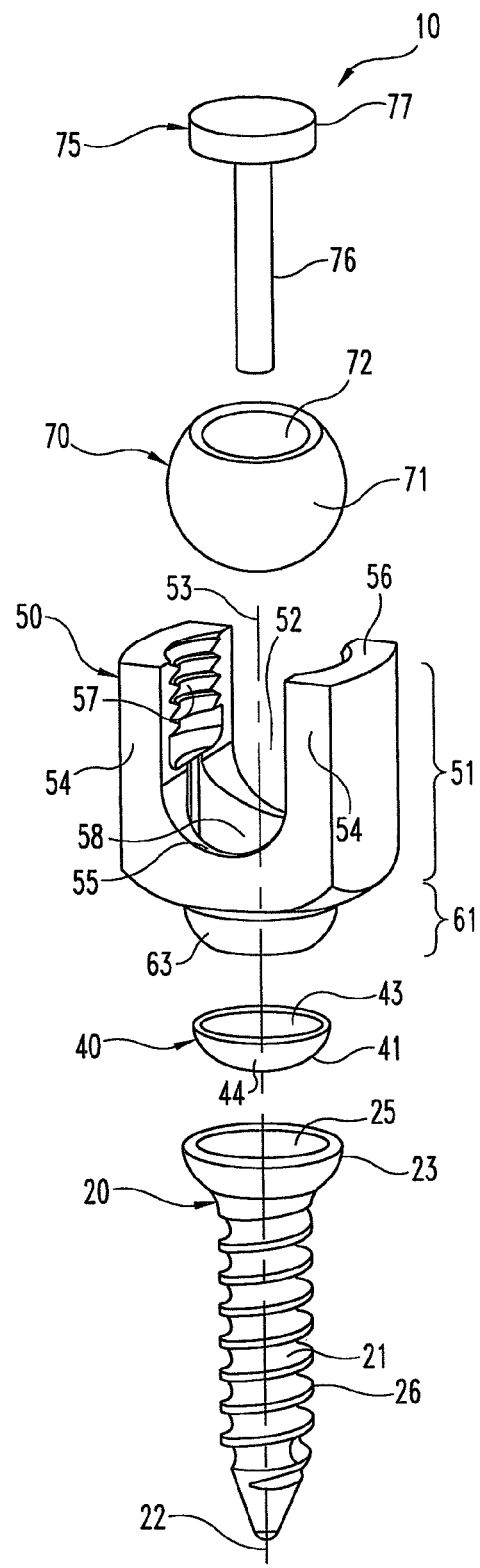
FIG. 2 is an exploded perspective view of an anchor assembly.
Figure 4:
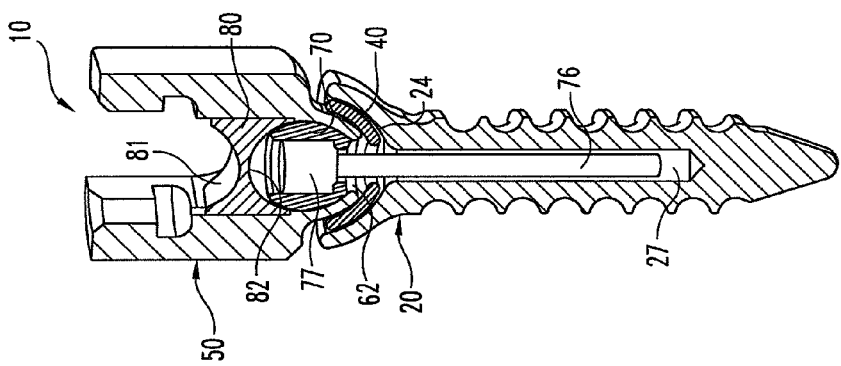
FIG. 4 is a perspective view in partial section of the anchor assembly of FIG. 2.
Figure 3:
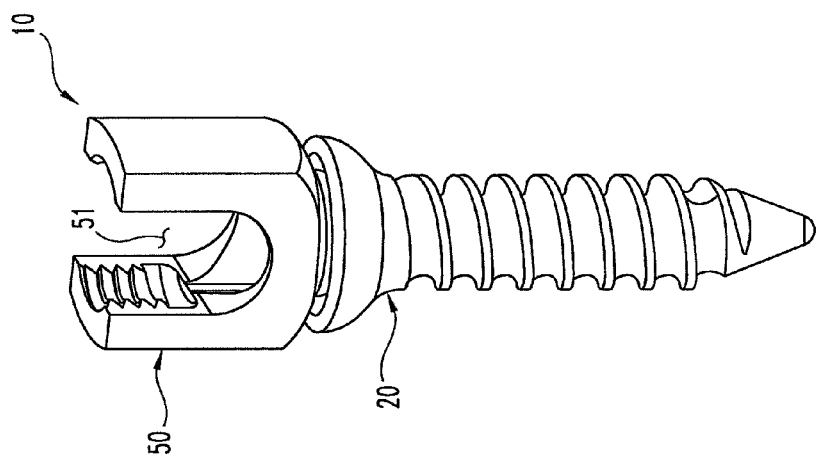
FIG. 3 is a perspective view of the anchor assembly of FIG. 2.

The threaded shaft 21 can be provided with self-drilling and/or self-tapping thread profile to facilitate insertion into bony tissue. In another embodiment, the threaded shaft is configured for insertion in a pre-drilled and pre-tapped hole in the vertebral body. Shaft 21 can be sized and shaped to engage a pedicle of a vertebral body, although other sizes and shapes are also contemplated. The specific choice of shaft features, such as thread pitch, shaft diameter to thread diameter ratio and overall shaft shape can vary, and the present application contemplates a wide variety of shaft designs Receiver 50 provides a coupling between anchor member 20 and connecting element 101. As shown in FIG. 2, receiver 50 has a top portion 51, also referred to as proximal portion 51, for engaging connecting element 101 and a bottom portion 61, also referred to as distal portion 61, for engaging anchor member 20. As shown in FIG. 2, top portion 51 of receiver 50 includes a U-shaped channel 52 which has an axis 53 and is delimited by two facing branches 54 that are spaced apart across channel 52 at a distance from each other. Channel 52 comprises a curvate bottom surface 55 which, for example, defines a semi-circular cross-section to receive the connecting element 101, and preferable features a diameter or other contour equivalent or otherwise complementary to that of the connecting element 101. The depth of channel 52 is such that connecting element 101, when positioned therein, may nest fully within channel 52, the top of connecting element 101 thereby being positioned substantially below the top surface 56 of receiver 50. This permits engaging member 90 (See FIGS. 6-8C) to be disposed on top of connecting element 101 in a manner described more fully hereinbelow. The cylindrical inside faces 57 of branches 54 are coaxial and at least partially threaded. Their thread is adapted to cooperate with that of engaging member 90. While branches 54 of receiver 50 are threaded on their inside faces 57, in other embodiments (not shown), threading can alternatively be provided on the outside faces of branches 54 for attachment of an engaging member having a form suitable for attachment to the outside surfaces of branches 54.

Bottom portion 61 of receiver 50 defines an opening 62 that opens into channel 52 through bottom surface 55 and provides a linear passage through bottom portion 61 that is contoured to receive and capture ferrule 70 and optionally crown 80 as further discussed hereinbelow. At its distal end, bottom portion 61 of receiver 50 defines a convex surface 63 that is formed to pivotally seat in cavity 25 of enlarged proximal end portion 23 of anchor member 20 with flexible member 40 positioned therebetween.

Figure 5A:
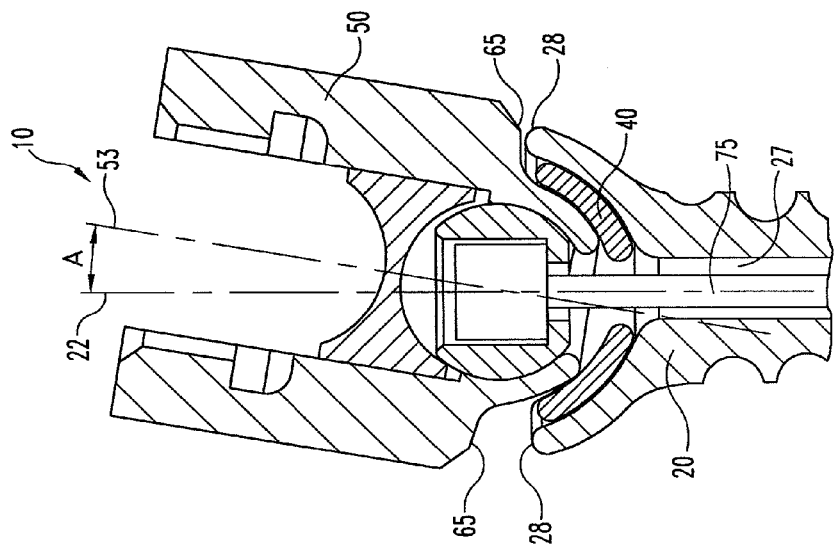
FIG. 5A is an elevation view in partial section of the anchor assembly of FIG. 2 with receiver in a first position relative to anchor member.
Figure 5B:
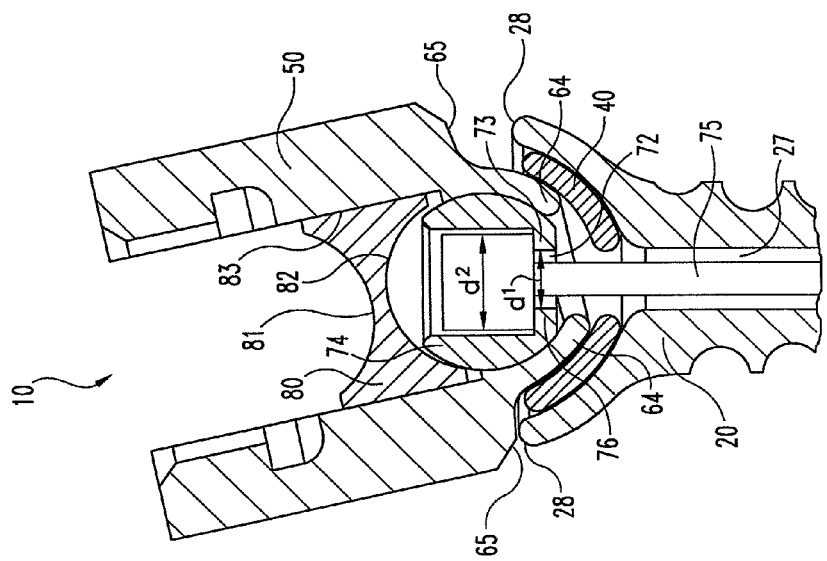
FIG. 5B is an elevation view in partial section of the anchor assembly of FIG. 2 with receiver in a second position relative to anchor member.

Flexible member 40 comprises a body 41 that has a shape corresponding to the contours of surface 63 of receiver 50 and surface 24 of anchor member 20, and is configured to be positioned between surfaces 63 and 24 upon assembly of anchor assembly 10. Flexible member 40 includes concave receiver-facing surface 43 and convex anchor member-facing surface 44, and also defines a central passage 42 therethrough. Prior to locking connecting element 101 to anchor assembly 10, multi-axial movement of receiver 50 relative to anchor member 20 is achieved by sliding movement of convex surface 63 of receiver 50 relative to concave receiver-facing surface 43 of flexible member 40, as best shown in FIGS. 5A and 5B. Flexible member 40 can optionally be affixed to surface 24 of anchor member 20, for example, using an adhesive or other type of bonding, to prevent sliding at the interface between flexible member 40 and anchor member 20 or, alternatively, such adhesive or other bonding can be absent.

In the embodiment shown in FIGS. 2-8C, receiver 50, flexible member 40 and anchor member 20 are coupled to one another using a ferrule 70 and tether 75 assembly. Ferrule 70 includes a generally spherical body 71 defining a central bore 72 therethrough. Central bore 72 has a first diameter d1 at its distal end portion 73 that is less than a second diameter d2 at its proximal end 74 portion, thereby forming a lip 76 for receiving and capturing head 77 of tether 75 when tether 75 is passed through bore 72 from a distal direction during assembly of anchor assembly 10. Spherical body 71 can be sized relative to U-shaped channel 52 of receiver 50 to nest within slot 58 formed into bottom surface 55 of channel 52 and to be retained in slot 58 by flanges 64 of the bottom portion 61 of receiver 50.

Receiver 50 is rotatably affixed to anchor member 20 with flexible member 40 therebetween by tether 75. Shaft 76 of tether 75 passes through bore 72 of ferrule 70, through opening 62 of receiver 50, through central passage 42 of flexible member 40 and into internal chamber 27 of shaft 21, where it is attached to shaft 21 to pivotally attach receiver 50 to anchor member 20 with a desired amount of tension. Attachment of tether 75 to shaft 21 can be accomplished in a wide variety of ways, non-limiting examples of which include staking, crimping, gluing or welding. With anchor assembly 10 assembled as such, the tension applied by tether 75 applies friction to the interface between convex surface 63 of receiver 50 and concave receiver-facing surface 43 of flexible member 40 and the interface between anchor member-facing surface 44 of flexible member 40 and inner concave surface 24 of anchor member 20. Surface 24 of enlarged proximal end portion 23 can optionally include teeth or other surface features (not shown) to enhance gripping of flexible member 40 when tension is applied by tether 75. In another embodiment (not shown), flexible member is absent, and anchor assembly is otherwise configured as shown. In this embodiment, the tension applied by tether 75 applies friction to an interface between convex surface 63 of receiver 50 and inner concave surface 24 of anchor member 20.

Anchor assembly 10 also includes a crown 80 positioned about the proximal end 74 of ferrule 70 in U-shaped channel 52 of receiver 50 when ferrule 70 is captured in receiver 50. Crown 80 can optionally be secured in place using staking or using a snap ring (not shown). Crown 80 includes a proximal end wall 81, a distal end wall 82 and a circumferential sidewall 83. Proximal end wall 81 forms a groove to receive connecting element 101 when it is captured in channel 52 of receiver 50. Distal end wall 82 includes a contour that receives and contacts proximal end 74 of ferrule 70. When anchor assembly 10 is assembled as shown in FIGS. 3-5B, receiver 50 is free to pivot and/or rotate relative to anchor member 20 by a sliding relationship between receiver flanges 64 against the outer wall of distal end 73 of ferrule 70 and against receiver-facing surface 43 of flexible member 40, together with a sliding relationship between distal end wall 82 of crown 80 and the outer wall of proximal end 74 of ferrule 70. The range of motion in this embodiment is limited by contact between edges 65 of receiver and edge 28 of anchor member 20, as shown in FIGS. 5A and 5B.

In one form anchor member 20, receiver 50, ferrule 70, crown 80 and engaging member are made of a rigid material, such as, for example, medical grade stainless steel, titanium, a titanium alloy or other metallic alloy, and/or a nonmetallic composition, such as, for example, a ceramic. Alternatively, these components can be made of a semi-rigid material, such as, for example, PEEK or a hard urethane composition.

Flexible member 40 can be made of, for example, a pliable polymer, such as, for example, a soft polyurethane composition or a silicone composition. Alternatively, flexible member 40 can be made from a semi-rigid material such as PEEK, flexible polyurethane or polypropylene, or can be made from a rigid material, such as, for example, medical grade stainless steel, titanium, a titanium alloy or other metallic alloy, and/or a nonmetallic composition that is formed into a spring. The softer materials would provide more motion of receiver 50 relative to anchor member 20. A semi-rigid material would provide a less rigid portion between two rigid pieces, providing a device with a less rigid interface between receiver 50/connecting element 101 and anchor member 20/bone. In embodiments in which flexible member 40 is made of a soft or semi-rigid material, the composition thereof can be selected or adapted to provide more or less resistance to motion, or more or resistance to fatigue.

Tether 75 can be made of multiple different materials, including, for example, wires of metal formed into a cable, braided strands of PEEK, a thin shaft of PEEK a braided form, cable form or thin shaft of other material. In addition, in alternate embodiments, tether 75 can be secured at both ends to ferrule 70 and shaft 21, respectively, or at either one of its ends. Securing tether 75 at only one end is expected to allow a greater degree of freedom for receiver 75 relative to embodiments in which both ends are secured.

As shown in FIGS. 5A and 5B, receiver 50 can be pivoted from a location along longitudinal axis 22 of anchor member 20 to an angle A or to any pivoted location therebetween. Accordingly, there is provided an infinite number of angular orientations between anchor member axis 22 and longitudinal axis 53 of receiver, the angular orientations defined by a cone having an apex at ferrule 70. Other embodiments contemplate that receiver 50 is pivotal in a single plane, or in selected planes, relative to anchor member 20. When anchor member 20 is engaged to the bony tissue, receiver 50 can be pivotally adjusted and repositioned as needed for engagement with connecting element 101 and to accommodate engagement of anchor assembly 10 with the vertebral anatomy.

Implantation of anchor assembly 10 is preceded by the proper preparation of the implantation site. For example, with a pedicle screw embodiment, a pre-drilled hole can be provided in the bone, into which it is desired that the anchor member 20 may be inserted. As stated above, at this point in the assembly process, crown 80 has not yet been forced downward against ferrule 70, and therefore rotational and polyaxial motion of receiver 50 relative to ferrule 70 is allowed. Once anchor member 20 is affixed to the appropriate prepared site, connecting element 101 is nested within channel 52, and disposed against proximal wall 81 of crown 80. Once the proper angulation of receiver 50 to anchor member 20 and the secure nesting of connecting element 101 in channel 52 of receiver 50 have been established, engaging member 90 is coupled to receiver 50 to hold connecting element 101 in place in channel 52.

FIGS. 6 and 7A show one embodiment engaging member 90 engageable with receiver 50 to secure connecting element 101 therein. Engagement member 90 can force the connecting element 101 distally along longitudinal axis 53 of receiver 50 and into contact with crown 80 when secured to the threads on inside faces 57 of top portion 51 of receiver 50. Engaging member 90 includes a proximal head portion 92 and a distal engaging portion 94. Engaging portion 94 can include external threads that threadingly engage threads on the inside faces 57 of top portion 51 of receiver 50. Engaging portion 94 is positionable into contact with connecting element 101 in channel 52 to force connecting element 101 against crown 80, thereby seating and substantially fixing receiver 50 in position, and arresting its motion, relative to ferrule 70.

In another engaging member embodiment depicted in FIG. 7B, engaging member 190 can be used in place of engaging member 90. Engaging member 190 includes head portion 192, which can be coupled with engaging portion 194 at a reduced thickness break-off region 196. When a threshold torque is applied to head portion 192, it severs from engaging portion 194 at break-off region 196. Should further tightening of engaging portion 194 be desired, or should it be desired to remove or loosen engaging portion 194, a driving instrument can be positioned into receptacle 198 to deliver the required rotational forces. Alternatively, a set screw, washer, crown, cap or other engaging member may be provided for engagement within and/or about receiver 50 to secure connecting element 101 thereto.

With engaging member 90, 190 tightened as described above, engaging member 90, 190 bears against connecting element 101, which bears against crown 80, which bears against ferrule 70, thereby rigidly affixing connecting element 101 to ferrule 70, and arresting movement of receiver 50 relative to ferrule 70. Because ferrule 70 is coupled to anchor member 20 under tension by tether 75, flanges 64 of receiver 50 are held against flexible member 40 and flexible member 40 is held against inner concave surface 24 of enlarged proximal end portion 23 of anchor member 20. In embodiments in which flexible member 40 is omitted (not shown), flanges 64 of receiver 50 are held against inner concave surface 24 of enlarged proximal end portion 23 of anchor member 20.

Figure 8C:
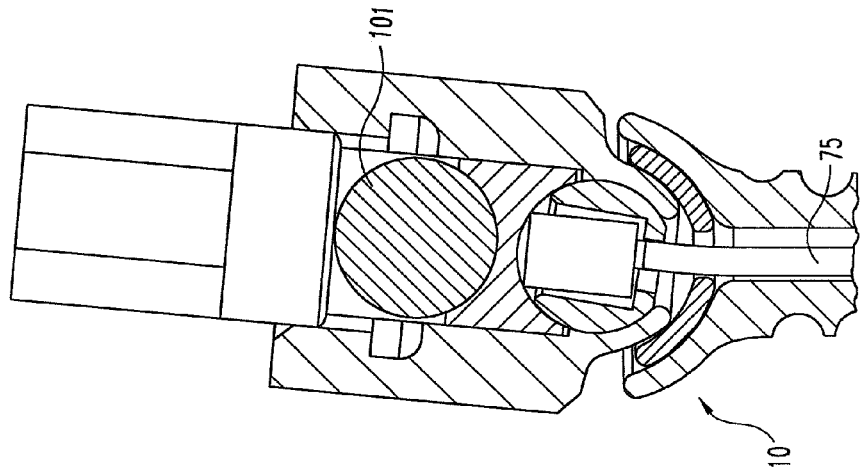
FIG. 8C is an elevation view in partial section of the anchor assembly of FIG. 2 with receiver in a third position relative to anchor member and with a connecting element coupled to receiver.
Figure 8B:
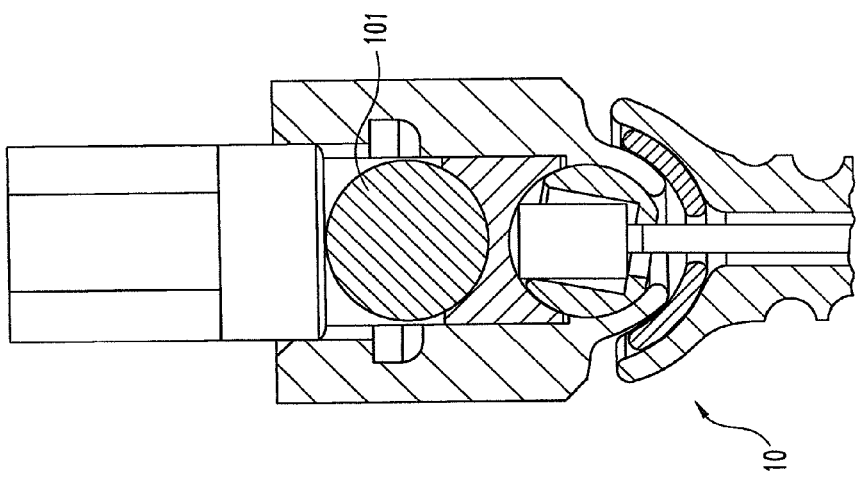
FIG. 8B is an elevation view in partial section of the anchor assembly of FIG. 2 with receiver in a second position relative to anchor member and with a connecting element coupled to receiver.
Figure 8A:
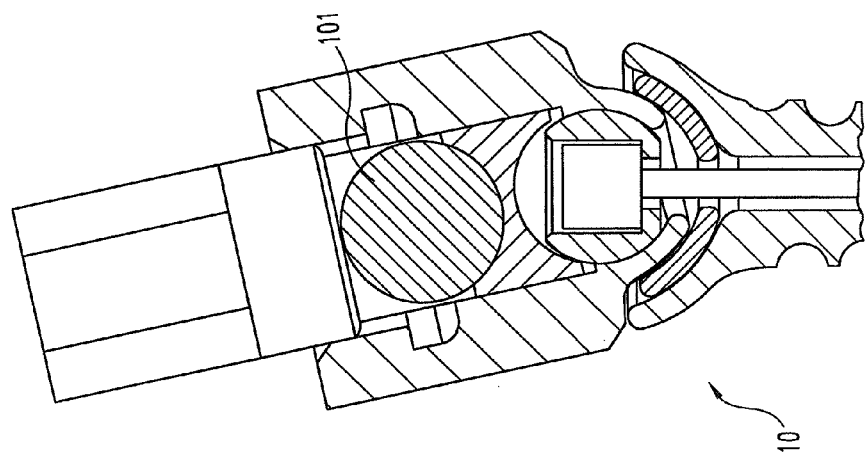
FIG. 8A is an elevation view in partial section of the anchor assembly of FIG. 2 with receiver in a first position relative to anchor member and with a connecting element coupled to receiver.

With connecting element 101 affixed to anchor assembly 10 in this manner, pivotal or rotation motion of receiver 50 relative to ferrule 70 is prevented; however, a secondary range of movement of receiver 50 relative to anchor member 20 is allowed upon application of stress forces on receiver 50, providing a flexible joint within anchor assembly 10 that allows limited movement after the multi-axial capability of anchor assembly 10 has been arrested. The secondary range of motion results from relative movement between ferrule 70 and anchor member 20. Such relative movement between ferrule 70 and anchor member can occur as a result of one or both of relative movement between ferrule 70 and head 77 of tether 75 or flexion and/or stretching of shaft 76 of tether 75, accompanied by flexion and/or compression of flexible member 40 (if present), as shown in FIGS. 8A-8C. FIG. 8A depicts a first unstressed position of receiver 50 relative to anchor member 20 after connecting element 101 is rigidly affixed to ferrule 70. FIG. 8B depicts a second angular position of receiver 50 relative to anchor member 20, wherein connecting element 101 is still rigidly affixed to ferrule 70 in the same orientation as shown in FIG. 8A; however, in FIG. 8B, ferrule 70 is angled relative to head 77 of tether 75. FIG. 8C depicts a third angular position of receiver 50 relative to anchor member 20, wherein connecting element 101 is still rigidly affixed to ferrule 70 in the same orientation as shown if FIGS. 8A and 8B; however, in FIG. 8C, in addition to angulation of ferrule 70 relative to head 77 of tether 75, shaft 76 of tether 75 is flexed to allow further angulation of receiver 50 relative to anchor member 20. Flexible member 40 (in embodiments in which it is present) can be deformed to allow the secondary range of motion. Flexible member 40 can then operate to return receiver 50 to its neutral position relative to anchor member 20 after a stress is removed. Tether 75 operates to restrict the maximum relative motion that is allowed between receiver 50 and anchor member 20. As will be understood by a person of ordinary skill in the art, in an embodiment in which tether 75 is formed of a rigid material, angulation of the type shown if FIG. 8B can be achieved, but not angulation of the type shown in FIG. 8C, which requires that tether 75 be formed of a flexible material.

While an embodiment anchor assembly 10 has been shown and described in detail above, the present application also contemplates anchor assemblies comprising a bone anchor, a receiver and a flexible member therebetween that have a wide variety of alternative configurations. For example, in various alternative embodiments, receiver 50 can be substituted for a receiver of alternate design, a wide variety of which are known. Examples of alternate receivers include, without limitation, receivers of a type commonly identified as an "open" receiver, a type commonly identified as a "closed" receiver, and a type commonly referred to as a "lateral connector." Moreover, these different types of receivers also can have a wide variety of forms. For example, open receivers can be of a type commonly referred to as a "top loading" receiver or a type commonly referred to as a "side loading" receiver.

The wording "open" receiver is used herein to describe a receiver that includes a pair of parallel proximally extending branches or arms which form a yoke with a U-shaped slot or channel to receive a rod or other connecting element. A connecting element is positioned in the U-shaped channel in generally perpendicular relation to the shank, and the open end of the yoke is closed off by a closure device. The closure device is tightened against the connecting element to clamp the connecting element in place against the bottom of the channel. The closure device secures the connecting element in place to prevent rotational or translational movement of the connecting element relative to the bone screw or other anchor member and the bone in which it is anchored. Conventional types of closure devices include a threaded plug which is screwed into threads formed into the surfaces forming the U-shaped channel or an outer nut that goes around and is threaded on the arms. For example, receiver 50 depicted in FIGS. 2-8C is an example of an "open" receiver.

The wording "closed" receiver is used herein to describe a receiver that includes a channel for receiving a rod or other connecting element, which channel is surrounded by the receiver body. Thus, the receiver must be pre-loaded onto the connecting element prior to instrumentation of the vertebra or an end of the connecting element must be passed through the channel during the implant procedure to place the connecting element in a desired relationship with the receiver. For example, in one embodiment, the receiver has a first bore extending along a first axis and a second bore extending along a second axis that intersects the first axis. The first and second bores are each completely encircled or surrounded by the receiver to capture the connecting element in the trans-axial bore. In one form, an engaging member is engageable to the receiver in the axial bore to further secure the connecting element with the anchor assembly. Since the trans-axial bore opens only on the opposite sides of the receiver, the elongate connecting element can be inserted through the trans-axial bore in an endwise fashion along an insertion axis that corresponds generally to the axis of the trans-axial bore. The connecting element can be moved in the patient along the insertion axis for engagement with one or more receivers of one or more other anchor assemblies.

The term "lateral connector" is used herein to describe a receiver in which the channel through which the rod or other connecting element passes does not transect the longitudinal axis of the anchor member, and thus the receiver is configured in such a way as to laterally offset the longitudinal axis of the anchor member relative to the channel passed through by the connecting element. Such a lateral connector with lateral offset is commonly made up of a component defining a channel through which the rod or other connecting element is intended to pass, which is connected by a lateral stem component to an anchor member or anchor-receiving member. Examples of lateral connectors are provided in U.S. Pat. No. 6,015,409, which is hereby incorporated by reference herein.

Figure 9:
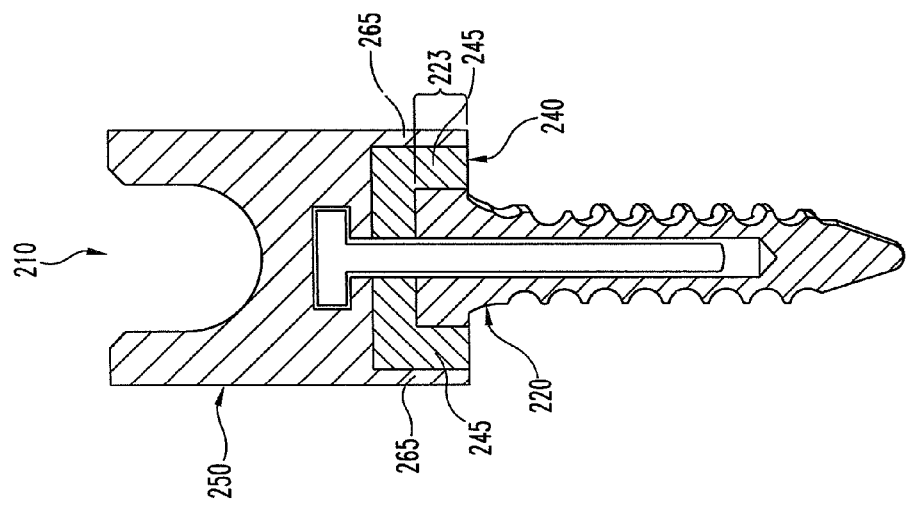
FIG. 9 is an elevation view in partial section of another embodiment anchor assembly.

The embodiments depicted in FIGS. 9-14 feature various alternative forms and arrangements for the connection of a receiver, a flexible member and a bone anchor. In FIGS. 9-14, receivers 150, 250, 350, 450, 550, 650 and anchor members 120, 220, 320, 420, 520, 620 are represented schematically, but can have a wide variety of forms as describe above in connection with receiver 50 and anchor member 20. In FIG. 9, there is depicted an embodiment anchor assembly 110 that includes anchor member 120, receiver 150 and flexible member 140 positioned therebetween. In this embodiment, anchor member 120 includes a proximal end portion 123 including flanges 29 defining a proximal end surface 130. Anchor-facing surface 144 of flexible member 140 is adjacent surface 130 of anchor member 120, and receiver-facing surface 143 of flexible member 140 is adjacent distal surface 163 of receiver 150. In the embodiment shown, flexible member 140 is generally washer-shaped and defines a bore therethrough for passage of shaft 176 of tether 175. The presence of flexible member 140 allows dynamic connection of anchor member 120 to a connecting element (not shown) rigidly coupled in channel 152 of receiver 150 due to the deformability of flexible member 120 under stresses. For example, under axial compression of receiver 150 toward anchor member 120, flexible member can be compressed to allow limited movement of receiver 150 toward anchor 120. In addition, under lateral pressure on receiver 150 a portion of flexible member can be deformed to allow limited angulation of receiver 150 relative to anchor member 120. The degree of movement allowed by anchor assembly 110 is dependent in part upon the thickness and compressability of flexible member 120. In addition, various features of tether 175 can provide limitations on the degree of movement allowed by anchor assembly 110. For example, the flexibility or rigidity of shaft 176 will bear on the amount of relative movement allowed, as will the relative size of head 177 of tether 175 compared to the size of recess 166 in which head 177 is captured.

Figure 10:
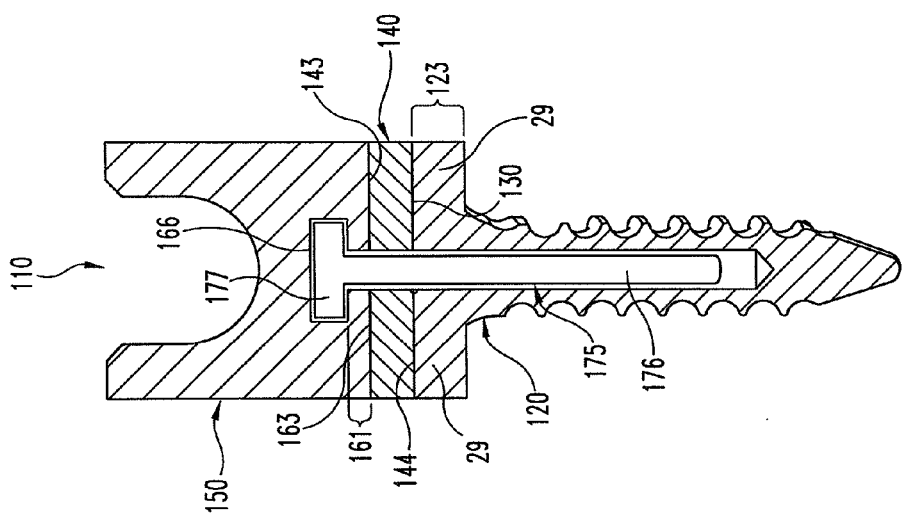
FIG. 10 is an elevation view in partial section of another embodiment anchor assembly.

In FIG. 10, there is depicted another embodiment anchor assembly 210 that includes anchor member 220, receiver 250 and flexible member 240 positioned therebetween. Proximal end portion 223 of anchor member 220 has a narrower profile than end portion 123 of anchor assembly 110 depicted in FIG. 9, and flexible member 240 has an inverted cup-shaped configuration with side portions 245 extending laterally and distally around end portion 123 of anchor member 120. In addition, receiver 250 includes distal flanges 265 that extend laterally and distally around flexible member 240. Similar to anchor assembly 110, the presence of flexible member 240 in anchor assembly 210 allows dynamic connection of anchor member 220 to a connecting element (not shown) rigidly coupled in channel 252 of receiver 250 due to the deformability of flexible member 220 under stresses. For example, under axial compression of receiver 250 toward anchor member 220, flexible member can be compressed to allow limited movement of receiver 250 toward anchor 220. In addition, under lateral pressure on receiver 250 a portion of flexible member can be deformed to allow limited angulation of receiver 250 relative to anchor member 220. The degree of movement allowed by anchor assembly 210 is dependent in part upon the thickness and compressability of flexible member 220. In addition, various features of tether 275 can provide limitations on the degree of movement allowed by anchor assembly 210. For example, the flexibility or rigidity of shaft 276 will bear on the amount of relative movement allowed, as will the size relative size of head 277 of tether 275 compared to the size of recess 266 in which head 277 is captured.

Figure 11:
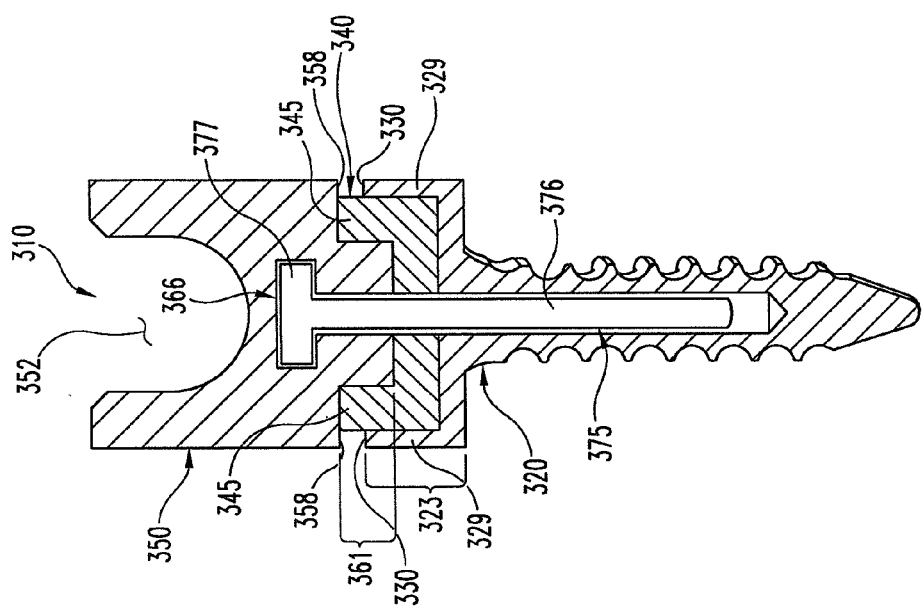
FIG. 11 is an elevation view in partial section of another embodiment anchor assembly.

In FIG. 11, there is depicted another embodiment anchor assembly 310 that includes anchor member 320, receiver 350 and flexible member 340 positioned therebetween. In assembly 310, anchor member 320 includes a proximal end portion 323 including flanges 329 extending laterally and proximally around flexible member 340 and defining proximal end surfaces 330. Bottom portion 361 of receiver 350 has a narrower profile than bottom portion 161 of anchor assembly 110 depicted in FIG. 9, and flexible member 340 has a cup-shaped configuration with side portions 345 extending laterally and proximally around bottom portion 361 of receiver 350. Proximal end surfaces 330 of flanges 329 are spaced apart from shoulder surfaces 358 of receiver 350 to allow for angulation of receiver 350 relative to anchor member 320. Similar to anchor assembly 110, the presence of flexible member 340 in anchor assembly 310 allows dynamic connection of anchor member 320 to a connecting element (not shown) rigidly coupled in channel 352 of receiver 350 due to the deformability of flexible member 320 under stresses. For example, under axial compression of receiver 350 toward anchor member 320, flexible member can be compressed to allow limited movement of receiver 350 toward anchor 320. In addition, under lateral pressure on receiver 350 a portion of flexible member can be deformed to allow limited angulation of receiver 350 relative to anchor member 320. The degree of movement allowed by anchor assembly 310 is dependent in part upon the thickness and compressability of flexible member 320. In addition, various features of tether 375 can provide limitations on the degree of movement allowed by anchor assembly 310. For example, the flexibility or rigidity of shaft 376 will bear on the amount of relative movement allowed, as will the size relative size of head 377 of tether 375 compared to the size of recess 366 in which head 377 is captured.

Figure 12:
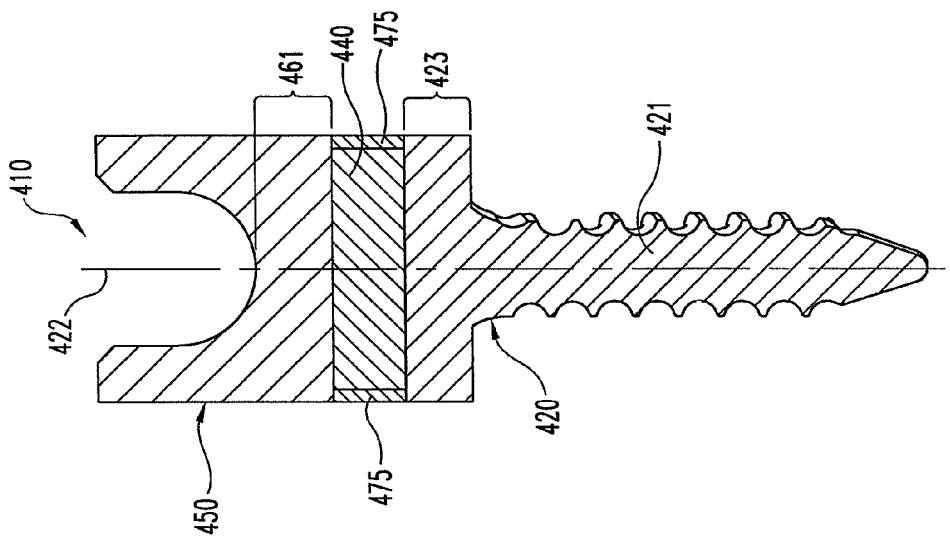
FIG. 12 is an elevation view in partial section of another embodiment anchor assembly.

In FIG. 12, there is depicted another embodiment anchor assembly 410 that includes anchor member 420, receiver 450 and flexible member 440 positioned therebetween. Assembly 410 has a configuration similar to that of assembly 110 depicted in FIG. 9; however, assembly 410 includes at least two tethers 475 positioned radially near the circumferential outer surfaces of receiver 450 and anchor member 420. Alternatively, the at least two tethers 475 can be substituted with a unitary tubular tether that extends around the entire circumference of flexible member 440. Assembly 410 can optionally include a central bore (not shown) through bottom portion 461 of receiver 450 and flexible member 440, and proximal end portion 423 of anchor member 420 can optionally include a recess (not shown) for receiving a driving tool for driving shaft 421 into a bony portion, said bore and said recess extending along a longitudinal axis 422 of shaft 421 and receiver 450.

Figure 13:
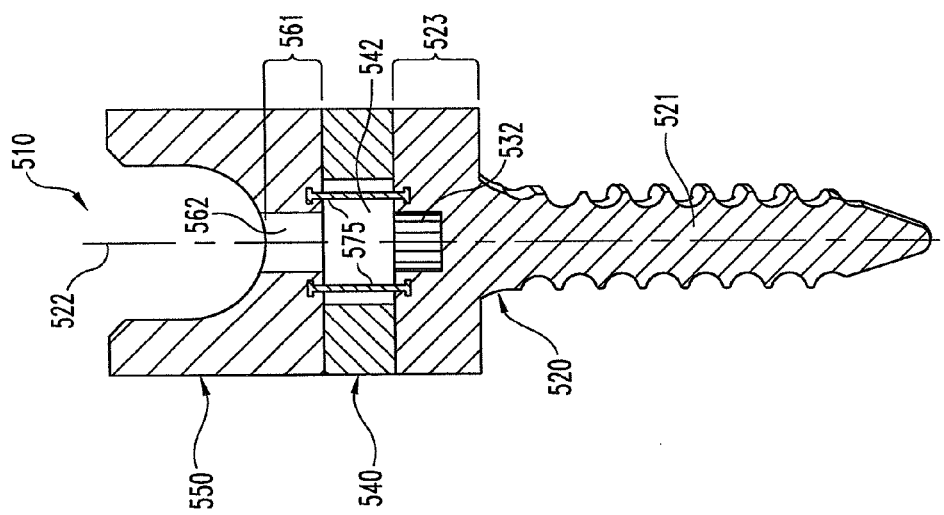
FIG. 13 is an elevation view in partial section of another embodiment anchor assembly.

In FIG. 13, anchor assembly embodiment 510 includes anchor member 520, receiver 550 and flexible member 540 positioned therebetween. Assembly 510 has a configuration similar to that of assembly 410 depicted in FIG. 12; however, assembly 510 includes a ring-shaped flexible member 540 extending between the circumferential surfaces of receiver 510 and anchor member 520, and at least two tethers 575 positioned centrally of said flexible member 540. Alternatively, the at least two tethers 575 can be substituted with a unitary tubular tether that extends around bore 561 and passage 542 on the axial side of flexible member 540. Central bore 562 extends axially through bottom portion 561 of receiver 450 and central passage 542 extends axially through flexible member 440. Proximal end portion 523 of anchor member 520 includes recess 532 for receiving a driving tool for driving shaft 521 into a bony portion. Bore 562, passage 542 and recess 532 extend along longitudinal axis 522 of shaft 521, flexible member 540 and receiver 550.

Figure 14:
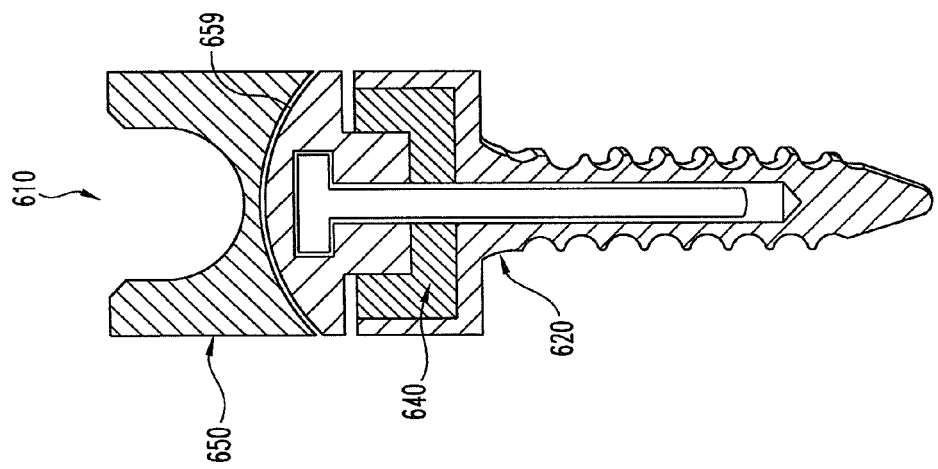
FIG. 14 is an elevation view in partial section of another embodiment anchor assembly.

In FIG. 14, anchor assembly 610 includes anchor member 620, receiver 650 and flexible member 640 positioned therebetween. Assembly 610 has a configuration similar to that of assembly 310 depicted in FIG. 11; however, receiver 650 includes a concave/convex interface 659 that allows multi-axial movement until a connecting element (not shown) is rigidly captured in channel 652, at which time movement at interface 659 is prevented.

In addition to tethering mechanisms for connecting a receiver to an anchor member as described above, a wide variety of alternate mechanisms for attaching a receiver to a bone anchor can be employed in accordance with the present application. Another anchor assembly embodiment 710, which employs an alternate attaching mechanism, is depicted in FIGS. 15-20. In assembly 710, anchor member 720 is coupled to a spherical collar 730 that is pivotally captured in receiver 750 so that receiver 750 can be pivoted relative to anchor member 720. Anchor member 720 includes an elongated shaft 721 extending along a longitudinal axis 722 and a head portion 723 having an outer generally cylindrical surface 724. Shaft 721 can include an outer thread profile 726 for threadingly engaging a bony structure to secure anchor assembly 710 thereto. The threaded shaft 721 can be provided with self-drilling and/or self-tapping thread profile to facilitate insertion into bony tissue. In another embodiment, the threaded shaft is configured for insertion in a pre-drilled and pre-tapped hole in the vertebral body. Shaft 721 can be sized and shaped to engage a pedicle of a vertebral body, although other sizes and shapes are also contemplated.

Figure 20:
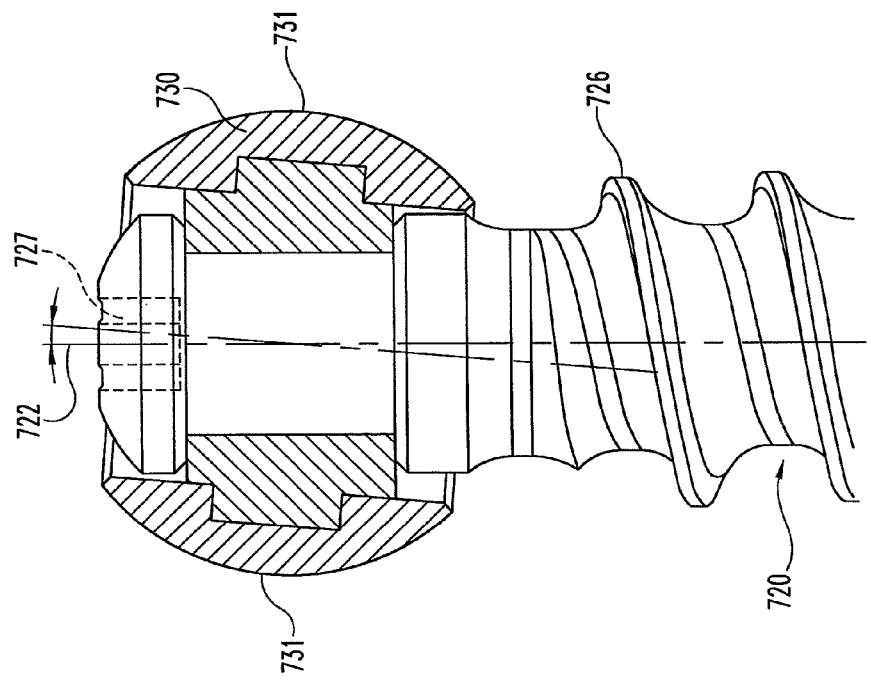
FIG. 20 is an elevation view of anchor member of the anchor assembly of FIG. 15 with a section view of collar and flexible member, and with collar positioned at an angle relative to anchor member.
Figure 19:
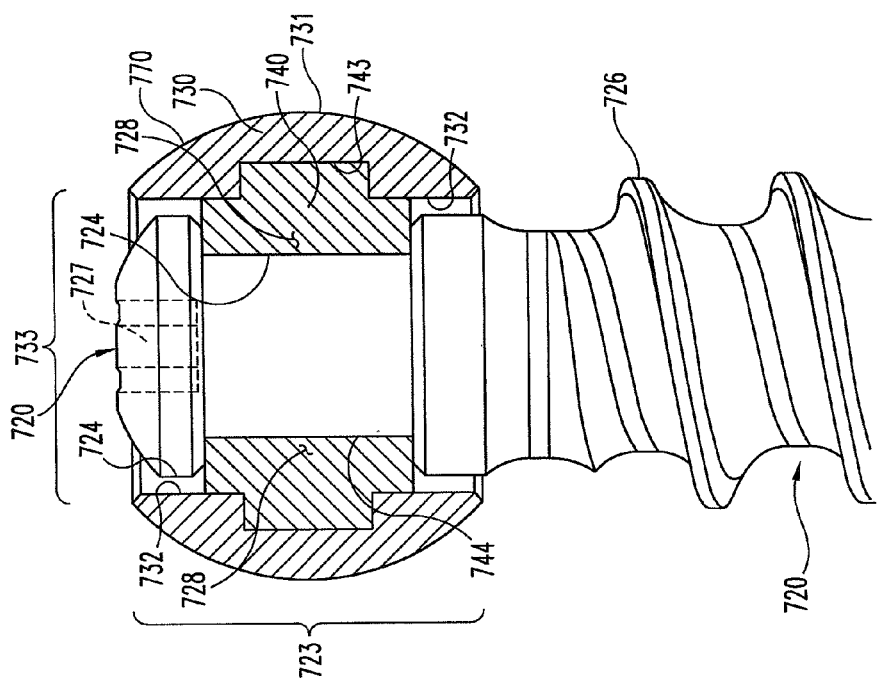
FIG. 19 is an elevation view of anchor member of the anchor assembly of FIG. 15 with a section view of collar and flexible member, and with collar and anchor member aligned coaxially.

With more particular reference to FIGS. 19 and 20, head portion 723 of anchor member 720 defines a recess 727 for accepting a driving tool such as a hexagonal screwdriver. Recess 727 defines a receiving locus for the application of a torque for driving anchor member 720 into a bony structure. It is preferable that recess 727 be co-axial with longitudinal axis 722 of anchor member 720, and most particularly with respect to shaft 721. Having the axes of recess 727 and shaft 721 co-linear facilitates insertion of anchor member 720 into the bony structure. Head portion 723 further includes a recessed channel 728 that extends around the circumference of head portion 723. Head portion 723 may instead be configured differently than that shown, such as with different contours and transition areas, as desired. Further, recess 727 may instead be an opening that is shaped differently than a hexagon, such as a slot or square, or may instead include a protruding element that can be manipulated by a tool. The specific shape of recess 727 may be chosen to cooperate with any suitable screw-driving tool. For example, recess 727 may comprise a slot for a flat-headed screwdriver, a crossed recess for a phillips head screwdriver, or most preferably, a hexagonally shaped hole for receiving an allen wrench.

Collar 730 has a generally semi-spherical outer surface 731 and an inner surface 732 that defines a central passage 733 having dimensions greater than the dimensions of outer surface 724 of anchor member 720. It is understood that the semi-spherical external shape of collar 730 is a section of a sphere which, in the embodiment shown, has a greater surface area than a hemisphere of equal radius, and it correspondingly exhibits an external contour which is equidistant from a center point of head portion 723. Collar 730 is configured to be coupled to head portion 723 of anchor member 720 by fitting over a generally tubular flexible member 740, which has a collar-facing outer surface 743 having contours complementary to the contours of inner surface 732 of collar 730. Flexible member 740 also has an anchor-facing inner surface 744 having contours complementary to the contours of outer cylindrical surface 724 of head portion 723 of anchor member 720. Surface 724 and/or 732 of head portion 723 and collar 730, respectively, can include teeth or other surface features (not shown) to enhance gripping of flexible member 740 when collar 730 is coupled to anchor member 720. With flexible member 740 positioned about head portion 723 and collar 730 positioned about flexible member 740, the combination has an outside appearance of an anchor with a semi-spherical head; however, collar 730 is dynamically attached to anchor member 720 by way of intermediate flexible member 740, which allows limited movement of collar relative to head when placed under stress, as discussed further hereinbelow.

Figure 18:
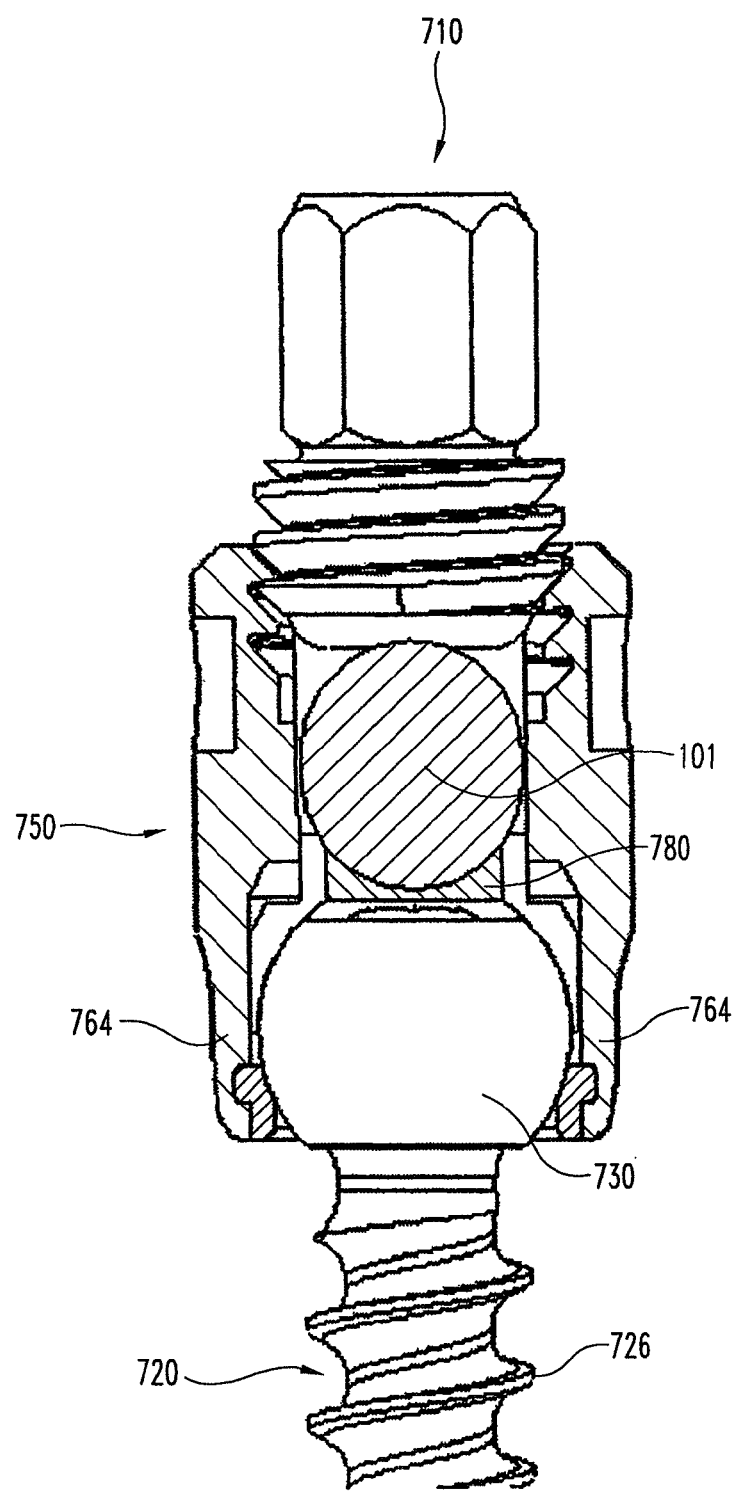
FIG. 18 is an elevation view in partial section of the anchor assembly of FIG. 15 with a connecting element coupled to receiver.

Anchor assembly 710 also includes a crown 780 positioned about the proximal end 734 of collar 730 to form the distal portion of U-shaped channel 752 of receiver 750. Crown 780 includes a proximal end wall 781, a distal end wall 782 and a circumferential sidewall 783. Proximal end wall 781 forms a groove to receive connecting element 101 when it is captured in channel 752 of receiver 750. Distal end wall 782 contacts proximal end 734 of collar 730. When anchor assembly 710 is assembled as shown in FIG. 18, receiver 750 is free to pivot and/or rotate relative to anchor member 720 by a sliding relationship between receiver flanges 764 against the outer wall of crown 730, together with a sliding relationship between distal end wall 782 of crown 780 and the outer wall of proximal end 734 of collar 730, as shown in FIG. 18. Accordingly, there is provided an infinite number of angular orientations between a longitudinal axis of anchor member 720 and a longitudinal axis of receiver 750, the angular orientations defined by a cone having an apex at head portion 723 of anchor member 720. Other embodiments contemplate that receiver 750 is pivotal in a single plane, or in selected planes, relative to anchor member 720. When anchor member 720 is engaged to the bony tissue, receiver 750 can be pivotally adjusted and repositioned as needed for engagement with connecting element 101 and to accommodate engagement of anchor assembly 710 with the vertebral anatomy. The range of motion in this embodiment is limited by contact between flanges 764 of receiver and shaft 721 of anchor member 720.

Crown 780 optionally includes a bore (not shown) therethrough in an axial direction to provide a linear passage through which a user may insert a driving tool to access the slot 727 in head portion 723 of anchor member 720 as head portion 723 resides in the interior chamber 762. Alternatively, in an embodiment in which crown 780 is absent, a driving tool can access slot 727 through an opening in the distal surface of top portion 751 of receiver 750.

Any alternative configurations of the head portion 723 and collar 730 should desirably be designed for compatibility with the inside of receiver 750 and crown 780 (if present), and also for compatibility with intermediate flexible member 740. That is, any variations of one of the components described herein should include a corresponding variation of any mating or connecting components to achieve the specific relationships between the elements of the invention as described.

Receiver 750 is rotatably affixed to crown 730 by receiving crown into a dimensioned chamber in bottom portion 761 of receiver 750. Bottom portion 761 of receiver 750 includes an anchor member head insertion opening 762, defined by annular lip 764, which forms the mouth of an interior chamber 765. In embodiment 710, annular lip 764 comprises a clip ring 766 that can be snap fit into a corresponding groove in bottom portion 761 to hold collar 730 within interior chamber 765. The diameter of opening 762 is more narrow than the maximum diameter of interior chamber 765. Interior chamber 765 is shaped to receive a semi-spherical shaped object.

In alternative embodiments, bottom portion 761 can include other features for achieving pivotal coupling with collar 730. For example, rather than including clip ring 766 for capturing collar 730 into chamber 765, bottom portion 761 can include a series of slots (not shown) which extend vertically upward from the distal edge 763 of receiver 750 to a point near the proximal side 767 of bottom portion 761. The slots are provided in this embodiment in order that the application of a deflecting force may widen or narrow opening 762 therein permitting the insertion of an object which is larger than the undeflected diameter of opening 762, or conversely, providing for the retention of an object which is smaller than the undeflected diameter of opening 762.

Top portion 751 of receiver 750 is configured similarly to top portion 51 of receiver 50 described hereinabove. A person of ordinary skill in the art will also appreciate that, in an embodiment that includes a closed receiver, such closed receiver would optionally include an axial bore extend through the top portion, through the crown (if present), and into the lower portion, to provide a linear passage through which a user may insert a driving tool to access the slot 727 in head portion 723 of anchor member 720 as head portion 723 resides in the interior chamber 762, and any other structural elements therein.

Prior to a surgical procedure, each receiver 750 to be used is premounted by clipping it onto collar 730, which is connected by flexible member 740 to head portion 723 of anchor member 720. Implantation of anchor assembly 710 is preceded by the proper preparation of the implantation site. For example, with a pedicle screw embodiment, a pre-drilled hole can be provided in the bone, into which it is desired that the anchor member 720 may be inserted. As stated above, at this point in the assembly process, crown 780 has not yet been forced downward against collar 730, and therefore rotational and polyaxial motion of receiver 750 relative to collar 730 is allowed. Anchor member 720 is implanted in the patient using an instrument inserted into slot 727. When anchor assembly 710 has been implanted, receiver 750 is free to rotate relative to anchor member 720. The receiver 750 and anchor member 720 are connected together by a ball-and-socket connection formed by collar 730 and chamber 762.

Once anchor member 720 is affixed to the appropriate prepared site, connecting element 101 is nested within channel 752, and disposed against proximal wall 781 of crown 780, as shown in FIG. 18. Once the proper angulation of receiver 750 to anchor member 720 and the secure nesting of connecting element 101 in channel 752 of receiver 750 have been established, engaging member 790 is coupled to receiver 750 to hold connecting element 101 in place in channel 752 and arresting movement between receiver 750 and collar 730, as shown in FIG. 18. Consequently, crown 780 (if present) or connecting element 101 (if crown 780 is absent) is locked onto collar 730, locking the anchor assembly 710 in position, rigidly immobilizing receiver 750 on collar 730. Engaging member 790 can have the form of engaging member 90, of engaging member 190, or other forms as would be contemplated by a person of ordinary skill in the art.

With engaging member 790 tightened as described above, engaging member 790 bears against connecting element 101, which bears against crown 780, which bears against collar 730, thereby rigidly affixing connecting element 101 to collar 730. Because collar 730 is coupled to anchor member 720 through flexible member 740, a secondary range of movement of receiver 750 relative to anchor member 720 is allowed upon application of stress forces on receiver 750, even though pivotal or rotational motion of receiver 750 relative to collar 730 is prevented. The secondary range of motion results from relative movement between collar 730 and anchor member 720. Moreover, because receiver 750 and connecting element 101 are locked onto collar 730, relative movement between collar 730 and anchor member 720 equates to relative movement between receiver 750/connecting element 101 and anchor member 720 as well. Such relative movement between collar 730 and anchor member can occur as a result of flexion and/or compression of flexible member 740, as shown in FIGS. 19 and 20. FIG. 19 depicts a first unstressed position of collar 730 relative to anchor member 720. Flexible member 740 can be deformed to allow the secondary range of motion.

Figure 21:
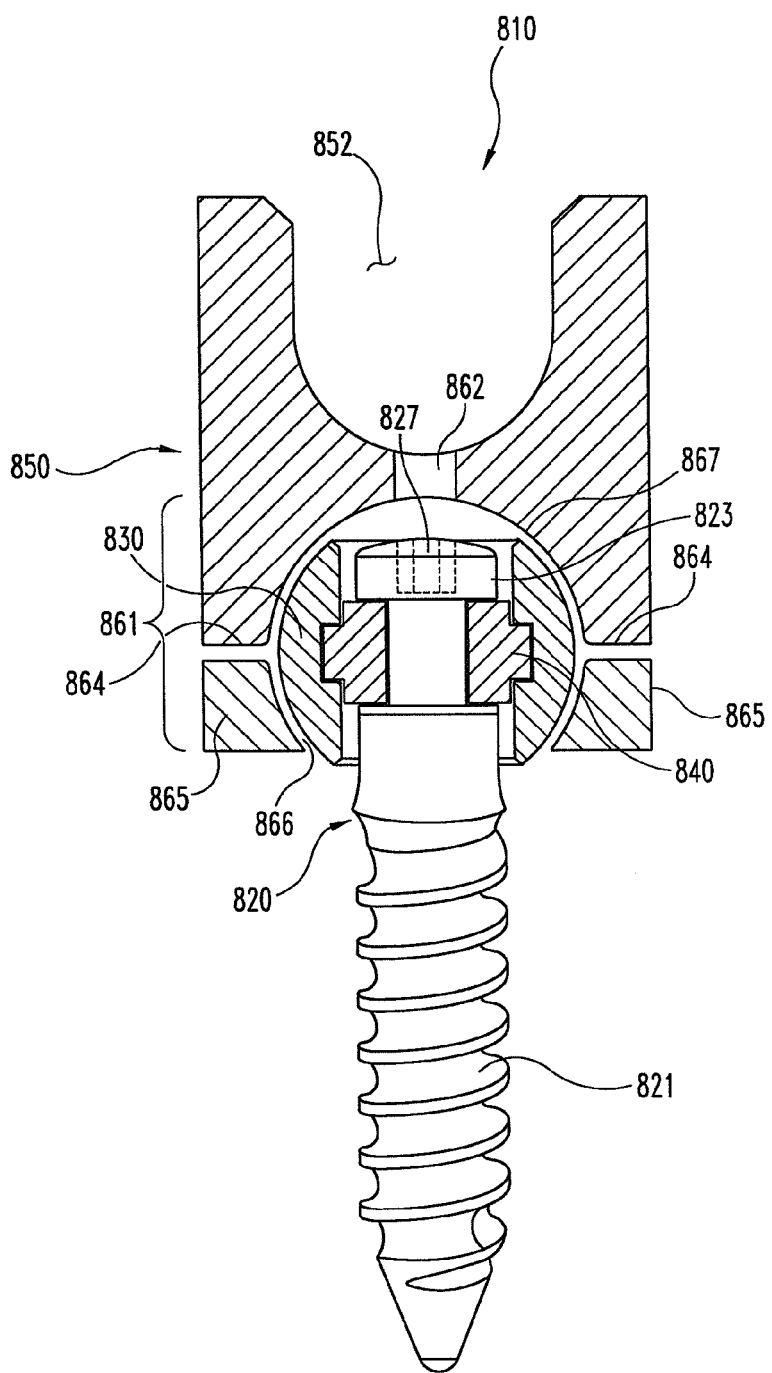
FIG. 21 is an elevation view in partial section of another embodiment anchor assembly.

In FIG. 21, there is depicted another embodiment anchor assembly 810 that includes anchor member 820, receiver 850, collar 830 and flexible member 840 positioned between anchor member 820 and collar 830. Assembly 810 has a configuration similar to that of assembly 710 depicted in FIGS. 15-20; however, in assembly 810, bottom portion 861 of receiver 850 is configured for a different manner of coupling to collar 830. More particularly, assembly 810 includes an annular bracket 865 defining passage 866. Passage 866 has a spherical surface with a contour that is complementary to the outer spherical surface of collar 830. To couple anchor member 820 to receiver 850, collar 830 is nested into a concave indentation 867 in bottom portion 861 of receiver 850, and bracket 865 is positioned distally into contact with collar 830 by passing bracket over shaft 821 of anchor member 820 such that shaft 821 of anchor member 820 passes through passage 866. Once bracket is positioned as shown in FIG. 21, bracket 865 is affixed to distal surfaces 864 of receiver 850 using set screws (not shown) or alternatively using clamps or other attachment mechanism. Bracket 865 can be attached to surfaces 864 without tightening, which allows rotational and polyaxial motion of receiver 850 relative to collar 830. Anchor member 820 can be implanted in a patient using an instrument inserted into through passage 862 in receiver 850 and into slot 827 formed in head portion 823 of anchor member 820.

When anchor assembly 810 has been implanted, receiver 850 is free to rotate relative to anchor member 820. After anchor member 820 is affixed to the appropriate prepared site, a connecting element (not shown) is nested within channel 852. Once the proper angulation of receiver 850 to anchor member 820 and the secure nesting of the connecting element (not shown) in channel 852 of receiver 850 have been established, an engaging member (not shown) can be coupled to receiver 850 to hold the connecting element in place in channel 752. In addition, screws or clamps (not shown) or other attachment mechanism employed to connect bracket 865 to surfaces 864 can be tightened to lock receiver 850 into a fixed position relative to collar 830. Because collar 830 is coupled to anchor member 820 through flexible member 840, a secondary range of movement of receiver 850 relative to anchor member 820 is allowed upon application of stress forces on receiver 850, even though pivotal or rotation motion of receiver 850 relative to collar 830 is prevented. The secondary range of motion results from relative movement between collar 830 and anchor member 820. Moreover, because receiver 850 and the connecting element fixed thereto are locked onto collar 830, relative movement between collar 830 and anchor member 820 equates to relative movement between receiver 850/connecting element and anchor member 820 as well. Such relative movement between collar 830 and anchor member can occur as a result of flexion and/or compression of flexible member 840.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. An attachment apparatus for attaching an elongated connecting element to a vertebral column, comprising:

an anchor member engageable to a vertebral body, said anchor member including a distal bone engaging portion and a proximal coupling portion configured to extend from the surface of the vertebral body, the anchor member further includes an axial chamber extending distally from and opening through said proximal coupling portion of said anchor member, said axial chamber extending into said bone engaging portion of said anchor member;

a receiver defining a channel configured to receive and engage an elongated connecting element and including a distal coupling portion; and a flexible member positioned between said receiver and said anchor member;

wherein a first of said proximal and distal coupling portions defines an inner cavity and a second of said proximal and distal coupling portions includes an end at least partially positioned within said inner cavity, said flexible member having a cup-shaped configuration defining an interior region, said flexible member positioned within said inner cavity with said end portion positioned within said interior region of said flexible member to provide a flexible interface between said anchor member and said receiver.

2. The attachment apparatus in accordance with claim 1 further comprising a component for attaching said receiver to said anchor member in an orientation whereby said proximal and distal coupling portions are spaced apart by said flexible member.

3. The attachment apparatus in accordance with claim 2 wherein said flexible interface between said receiver and said anchor member allows multi-axial motion of said receiver relative to said anchor member.

4. The attachment apparatus in accordance with claim 2 wherein said component for attaching said receiver to said anchor member comprises a tether.

5. The attachment apparatus in accordance with claim 4 wherein said tether comprises a member selected from the group consisting of wires of metal formed into a cable, braided strands of PEEK, a thin shaft of PEEK and a braided form, cable form or thin shaft of other material.

6. The attachment apparatus in accordance with claim 4, wherein said distal bone engaging portion of said anchor member comprises an elongate externally threaded shaft; wherein said tether further comprises a ferrule defining a bore therethrough and having a spherical outer surface seated in a complementary cavity in said receiver; wherein a shaft portion of said tether extends distally from said bore of said ferrule and is captured in said axial chamber of said anchor member; and wherein said bore is configured to capture a head portion of said tether, thereby attaching said receiver to said bone anchor.

7. The attachment apparatus in accordance with claim 6 wherein said flexible member is effective to allow relative movement between said receiver and said anchor member after said ferrule and said receiver are locked together, arresting multiaxial movement between said ferrule and said receiver.

8. The attachment apparatus in accordance with claim 6 wherein said receiver comprises two proximal arms extending around and defining said channel and having channel-facing surfaces that define thread-receiving grooves, said attachment apparatus further comprising a threaded fastener structured to engage said grooves to secure the connecting element in the channel between the fastener and the ferrule.

9. The attachment apparatus in accordance with claim 8, further comprising a crown positioned between said connecting element and said ferrule, said crown having a distal surface having a contour complimentary to a proximal surface of said ferrule and having a proximal surface having a contour complimentary to said connecting element.

10. The attachment apparatus in accordance with claim 1 wherein said proximal coupling portion of said anchor member has a proximal receiver-facing surface and defines an axial chamber opening through said receiver-facing surface; wherein said distal coupling portion of said receiver has a distal anchor member-facing surface and defines an axial chamber opening through said anchor member-facing surface; and wherein said flexible member is positioned between said distal anchor member-facing surface of said receiver and said proximal surface of said anchor member and defines a central passage therethrough; said attachment apparatus further comprising a tether extending from said axial chamber of said receiver, through said central passage of said flexible member and into said axial chamber of said anchor member for attaching said receiver to said anchor member in an orientation whereby said distal anchor member-facing surface of said receiver faces said proximal receiver-facing surface of said anchor member in an opposing relationship spaced apart by said flexible member.

11. An attachment apparatus for attaching an elongated connecting element to a vertebral column, comprising:
    an anchor member engageable to a vertebral body, said anchor member including a distal bone engaging portion and a proximal end portion configured to extend from the surface of the vertebral body;
    a receiver defining a channel configured to receive and engage an elongated connecting element; and
    a flexible member positioned at an interface between said receiver and said anchor member; and
    wherein said anchor member has a proximal receiver-facing surface; wherein said receiver has a distal anchor member-facing surface; and wherein said flexible member is positioned between said distal surface of said receiver and said proximal surface of said anchor member; said attachment apparatus further comprising a tether extending from a circumferential edge of said distal surface of said receiver to a circumferential edge of said proximal surface of said anchor member for attaching said receiver to said anchor member in an orientation whereby said distal surface of said receiver faces said proximal surface of said anchor member in an opposing relationship spaced apart by said flexible member.

12. The attachment apparatus in accordance with claim 11 further comprising a component for attaching said receiver to said anchor member in an orientation whereby said proximal and distal coupling portions are spaced apart by said flexible member.

13. The attachment apparatus in accordance with claim 12 wherein said flexible interface between said receiver and said anchor member allows multi-axial motion of said receiver relative to said anchor member.

14. The attachment apparatus in accordance with claim 11, wherein said distal bone engaging portion of said anchor member comprises an elongate externally threaded shaft; wherein said component for attaching said receiver to said anchor member comprises a tether, wherein said tether further comprises a ferrule defining a bore therethrough and having a spherical outer surface seated in a complementary cavity in said receiver; wherein a shaft portion of said tether extends distally from said bore of said ferrule and is captured in said axial chamber of said anchor member; and wherein said bore is configured to capture a head portion of said tether, thereby attaching said receiver to said bone anchor.

15. The attachment apparatus in accordance with claim 14 wherein said flexible member is effective to allow relative movement between said receiver and said anchor member after said ferrule and said receiver are locked together, arresting multiaxial movement between said ferrule and said receiver.

16. The attachment apparatus in accordance with claim 1 wherein said proximal coupling portion of said anchor member has a proximal receiver-facing surface; wherein said distal coupling portion of said receiver has a distal anchor member-facing surface; and wherein said flexible member comprises an annular body defining a central passage therethrough, said flexible member positioned between a peripheral portion of said distal anchor member-facing surface of said receiver and a peripheral portion of said proximal receiver-facing surface of said anchor member; said attachment apparatus further comprising a tether extending through said central passage of said flexible member from said distal anchor member-facing surface of said receiver to said proximal receiver-facing surface of said anchor member for attaching said receiver to said anchor member in an orientation whereby said distal anchor member-facing surface of said receiver faces said proximal receiver-facing surface of said anchor member in an opposing relationship spaced apart by said flexible member.

17. The attachment apparatus in accordance with claim 16 wherein said anchor member defines a recess that opens through said proximal receiver-facing surface for receiving a driving tool; and wherein said receiver defines an axial passage configured to allow passage of a driving tool.

18. The attachment apparatus in accordance with claim 1 wherein said flexible member is made of a composition selected from the group consisting of a pliable polymer, a semi-rigid material and a rigid material formed into a spring.

19. The attachment apparatus in accordance with claim 1 wherein said flexible member is made of a composition selected from the group consisting of a soft polyurethane composition, a silicone composition, PEEK, polypropylene, medical grade stainless steel, titanium, a titanium alloy, other metallic alloy and a rigid nonmetallic composition.

20. The attachment apparatus in accordance with claim 1 wherein said end portion defined by said second of said proximal and distal coupling portions defines a convex outer surface, said flexible member defining a complementary concave inner surface interfacingly engaged with said convex outer surface of said end portion.

21. The attachment apparatus in accordance with claim 20 wherein said inner cavity defined by said first of said proximal and distal coupling portions defines a concave inner surface, said flexible member defining a complementary convex outer surface interfacingly engaged with said concave inner surface of said inner cavity.

22. An attachment apparatus for attaching an elongated connecting element to a vertebral column, comprising:
an anchor member engageable to a vertebral body, said anchor member including a distal bone engaging portion and a proximal coupling portion configured to extend from the surface of the vertebral body, the bone engaging portion includes an axial chamber extending distally from and opening through the proximal coupling portion of the anchor member, the axial chamber extending into the bone engaging portion of the anchor member;
a receiver defining a channel configured to receive and engage an elongated connecting element; and
a flexible member positioned at an interface between said receiver and said anchor member; and
wherein said flexible member comprises an annular body disposed about said proximal head portion of said anchor member; and wherein a collar is disposed about said flexible member, said collar having a semi-spherical outer surface configured to be coupled to said receiver.

23. The attachment apparatus in accordance with claim 22 wherein said receiver comprises a chamber at its distal end dimensioned to receive said collar and pivotally capture said collar in said chamber.

24. The attachment apparatus in accordance with claim 22 wherein said anchor assembly further includes a crown positioned about a proximal end of said collar and forming a distal portion of a U-shaped channel in said receiver.

25. The attachment apparatus in accordance with claim 22 wherein said flexible member is effective to allow relative movement between said receiver and said anchor member after said collar and said receiver are locked together, arresting multiaxial movement between said collar and said receiver.

26. A system for stabilizing a bony segment, comprising:
an elongated connecting element; and
an anchoring assembly engageable to said connecting element, wherein said anchoring assembly comprises:
an anchor member having a distal bone engaging portion engageable to the bony segment and a proximal coupling portion, the bone engaging portion includes an axial chamber extending distally from and opening through the proximal coupling portion of the bone anchor, the axial chamber extending into the bone engaging portion of the anchor member;
a receiver member extending along a receiver axis, said receiver member defining a channel for receiving said connecting element along any one of a plurality of implantation axes that are transverse to said receiver axis, said receiver member including a distal coupling portion;
a flexible member positioned between said receiver member and said anchor member, wherein a first of said proximal and distal coupling portions defines an inner cavity and a second of said proximal and distal coupling portions includes an end portion at least partially positioned within said inner cavity, said flexible member having a cup-shaped configuration defining an interior region, said flexible member positioned within said inner cavity with said end portion positioned within said interior region of said flexible member to provide a flexible interface between said anchor member and said receiver member; and
a securing member engageable to said receiver member to secure said connecting element in said receiver member.

27. The system of claim 26 wherein said end portion defined by said second of said proximal and distal coupling portions defines a convex outer surface, said flexible member defining a complementary concave inner surface interfacingly engaged with said convex outer surface of said end portion.

28. The system of claim 27 wherein said inner cavity defined by said first of said proximal and distal coupling portions defines a concave inner surface, said flexible member defining a complementary convex outer surface interfacingly engaged with said concave inner surface of said inner cavity.

29. A system for stabilizing a bony segment, comprising:
an elongated connecting element; and
an anchoring assembly engageable to said connecting element, wherein said anchoring assembly comprises:
an anchor member engageable with the bone segment comprising a distal bone engaging portion and a proximal coupling portion configured to extend from a surface of the bony segment, the anchor member having an axial chamber therein extending distally from and opening through the coupling portion of the anchor member, the axial chamber extending into the bone engaging portion of the anchor member;
a receiver member coupled to said anchor member and extending proximally therefrom along a receiver axis, said receiver member defining a channel for receiving said connecting element along any one of a plurality of implantation axes that are transverse to said receiver axis;
a flexible member positioned at an interface between said receiver and said anchor member; and a securing member engageable to said receiver member to secure said connecting element in said receiver member, wherein said securing member includes a receiver engaging portion threadingly engageable with said receiver member and a proximal break-off portion removable from said receiver engaging portion upon application of a threshold torque to said break-off portion.

* * * * *